(12) United States Patent
Sellier et al.

(10) Patent No.: US 8,642,024 B2
(45) Date of Patent: Feb. 4, 2014

(54) COSMETIC COMPOSITION COMPRISING AT LEAST ONE ORGANIC STRUCTURING AGENT, AT LEAST ONE ABSORBENT MIXTURE AND AT LEAST ONE SURFACTANT FOR APPLICATION TO KERATIN MATERIALS

(75) Inventors: Céline Sellier, Paris (FR); Gérard Gabin, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/945,222

(22) Filed: Nov. 12, 2010

(65) Prior Publication Data
US 2011/0142788 A1    Jun. 16, 2011

Related U.S. Application Data

(60) Provisional application No. 61/264,295, filed on Nov. 25, 2009.

(30) Foreign Application Priority Data

Nov. 13, 2009 (FR) ...................................... 09 58027

(51) Int. Cl.
*A61K 31/74* (2006.01)
(52) U.S. Cl.
USPC ........................................ 424/78.18; 514/60
(58) Field of Classification Search
None
See application file for complete search history.

(56) References Cited

U.S. PATENT DOCUMENTS

| | | | |
|---|---|---|---|
| 5,763,500 A | 6/1998 | Roulier et al. | |
| 5,925,380 A | 7/1999 | Roulier et al. | |
| 6,303,108 B1 | 10/2001 | Roulier et al. | |
| 2007/0009456 A1 | 1/2007 | Delacour et al. | |

FOREIGN PATENT DOCUMENTS

| | | | | |
|---|---|---|---|---|
| EP | 0 745 378 A1 | 12/1996 | | |
| EP | 0 745 379 A1 | 12/1996 | | |
| EP | 0 968 703 A1 | 1/2000 | | |
| EP | 0968703 A1 * | 1/2000 | ............... | A61K 7/00 |
| EP | 1 106 165 A1 | 6/2001 | | |
| FR | 2 555 441 A1 | 5/1985 | | |
| FR | 2 779 649 A1 | 12/1999 | | |

OTHER PUBLICATIONS

French Search Report for FR 0958027, dated Jul. 13, 2010.
English language abstract of EP 0 968 703 A1, Jan. 5, 2000.
English language abstract of EP 1 106 165 A1, Jun. 13, 2001.
English language abstract of FR 2 555 441 A1, May 31, 1985.

* cited by examiner

*Primary Examiner* — Lezah Roberts
*Assistant Examiner* — Nannette Holloman
(74) *Attorney, Agent, or Firm* — O'Brien Jones, PLLC

(57) ABSTRACT

Provided herein is an anhydrous cosmetic composition comprising at least one organic structuring agent, at least one modified starch, at least one wood meal, at least one surfactant, and at least one anhydrous liquid phase. Also provided is a method for cleansing and/or conditioning keratin materials, comprising applying at least one of the anhydrous cosmetic compositions to the keratin materials.

17 Claims, No Drawings

COSMETIC COMPOSITION COMPRISING AT LEAST ONE ORGANIC STRUCTURING AGENT, AT LEAST ONE ABSORBENT MIXTURE AND AT LEAST ONE SURFACTANT FOR APPLICATION TO KERATIN MATERIALS

This application claims benefit of U.S. Provisional Application No. 61/264,295, filed Nov. 25, 2009. This application also claims benefit of priority under 35 U.S.C. §119 to French Patent Application No. 0958027, filed Nov. 13, 2009.

Disclosed herein is an anhydrous cosmetic composition comprising at least one organic structuring agent, at least one mixture of two different types of absorbent, at least one surfactant and at least one anhydrous liquid phase, and also disclosed is a method for cleansing and/or conditioning keratin materials (skin and/or hair).

Standard care products for keratin materials, for example hair conditioners or masks, can be in the form of more or less viscous creams. Similarly, cleansing products for keratin materials, such as the hair, can be in the form of more or less viscous liquids.

However, these products may have a tendency to escape between the fingers or to escape from their conditioning, which may be a great inconvenience when they come into contact with clothing, for example during movements. Furthermore, they may require the presence of a preserving agent in order to ensure the microbiological quality of the product.

Document EP 0 968 703 discloses a deformable solid cosmetic or dermatological composition, comprising a structuring agent, an organic absorbent and optionally a surfactant liquid phase. This composition may be used, for example, for the cosmetic treatment of the hair.

It is beneficial to overcome at least one of the drawbacks that may be associated with aforementioned products.

Thus, at least one aspect of the present disclosure is an anhydrous cosmetic composition comprising at least one organic structuring agent, at least one modified starche, at least one wood meal, at least one surfactant, and at least one anhydrous liquid phase.

The term "anhydrous composition" means a composition that comprises no water (0%) or that has a water content of less than 5% by weight, such as less than 2% by weight and further such as less than 1% by weight, relative to the total weight of the composition. It should be noted that the water may also be in the form of bound water, for instance the water of crystallization of salts, or of traces of water absorbed by the starting materials used in the production of the compositions as disclosed herein.

The term "anhydrous liquid phase" means a liquid phase that comprises no water (0%) or that has a water content of less than 5% by weight, such as less than 2% by weight and further such as less than 1% by weight, relative to the total weight of the liquid phase.

The composition as disclosed herein may have an entirely unusual texture. The texture can be of very low specific gravity, for example, ranging from 0.3 to 0.8, and may have a very soft feel. It may be in a form ranging from whipped cream to a more or less firm, non-tacky modelable solid.

The solid nature of the composition as disclosed herein may allow for easy handling and easy transportation of the product. Since the texture can be very modelable, the composition can be very easy to measure out and to apply. The composition may be easily divided up in the hand so as to take only the necessary amount of the product. For example, this composition may be conditioned in single-dose form, such as in the form of small cubes or single-dose packs.

Furthermore, the composition may break down quickly and easily upon contact with a liquid, such as an aqueous liquid.

As disclosed herein, the term "breaking down" means breaking down with the aid of a liquid rather than breaking down on touching, as is the case for certain makeup compositions such as eye shadows that can be taken up with the fingers or using a brush. This liquid-mediated breakdown may correspond to destructuring of the solid, with dissolution or dispersion of the particles in the liquid.

The composition as disclosed herein can be very easy to rinse out and thus requires relatively little water to do so.

The composition as disclosed herein can be also very comfortable to apply. According to at least one embodiment, no running of the composition is observed, unlike standard compositions, which may run the risk of irritating for example the face and the eyes. The absence of running can be highly appreciated in the case of permanent waving and dyeing, and also in the case of shampoos for children.

The structure of the composition as disclosed herein, which can be a hindered matrix of granular type, can allow the formulation of products comprising starting materials, such as fatty substances, in high percentages and for example greater than 15% by weight of the composition, which may not be easy with standard structures.

Furthermore, the anhydrous nature of the composition can make it possible to avoid the use of preserving agents.

The composition as disclosed herein may also have a heating effect when dispersed in aqueous medium. It may also have a foaming effect depending on the nature and concentration of the at least one surfactant introduced.

Finally, the composition as disclosed herein can give a soft feel on keratin materials, such as the hair, and a styling effect on dried hair.

The at least one organic structuring agent (also known as texturing agent) present in the composition as disclosed herein comprises, for example, at least one type of particle. According to at least one embodiment, the at least one type of particle is chosen from rigid particles that can be insoluble in the medium. The at least one organic structuring agent can be chosen from compounds that have the characteristic of being able to be removed easily from keratin materials upon contact with pure water or with water comprising polar compounds.

The following test serves as a guideline for selecting the at least one structuring agent without limiting the scope thereof:
  mixing the at least one type of test particle with water comprising a common dye, until a colored paste is obtained,
  adding a drop of pure water or of water comprising 10% of at least one compound chosen from ethanol, propylene glycol and sodium lauryl sulfate to the paste thus prepared.

When the paste at the point of impact of the drop is much clearer than the rest of the paste, this means that the at least one type of test particle is a candidate to be the at least one structuring agent; conversely, when the paste at the point of impact does not become discolored, the at least one type of test particle is unsuitable.

In order to obtain a solid with, for example, a soft and pleasant feel, the at least one type of particle may have a mean particle size ranging from 1 to 300 microns (µm), for example from 5 to 200 µm, such as from 10 to 100 µm and further such as from 15 to 40 µm.

In order to give the composition as disclosed herein, for example, a light and airy appearance, the at least one type of particle may have a specific gravity of less than 0.1, such as less than 0.09, further such as less than 0.06 and even further such as less than 0.04.

In order to obtain this low density, hollow particles optionally filled with at least one gas can be used. The at least one gas may, for example, be chosen from air, nitrogen, isobutane and isopentane.

According to at least one embodiment, the at least one type of particle can be in the form of beads. It is possible, however, to use at least one type of particle in the form of fibers or needles.

These particles may be made form various inert materials that do not react chemically with the medium; for example, these particles do not react with the oils, surfactants, water and the various other constituents of the composition.

The at least one type of particle can be chosen from particles of thermoplastic materials chosen from polyamides, such as Nylon, polymers comprising at least one monomer chosen from acrylonitrile, vinylidene chloride, vinyl chloride, optionally expanded acrylic, and optionally expandable styrene monomer, and microporous microspheres.

The acrylic monomer is, for example, a methyl or ethyl acrylate or methacrylate. The styrene monomer is, for example, α-methylstyrene or styrene.

The ORGASOL particles sold by the company Atochem may be used as Nylon particles. These particles are porous solid spheres with a diameter ranging from 5 μm to 60 μm.

According to at least one embodiment, the at least one type of particle can be chosen from deformable hollow particles of an expanded copolymer of vinylidene chloride and acrylonitrile, and deformable hollow particles of an expanded copolymer of vinylidene chloride, acrylonitrile, and (meth)acrylate or styrene monomer. For example, a polymer comprising 0-60% of units derived from vinylidene chloride, 20-90% of units derived from acrylonitrile, and 0-50% of units derived from an acrylic or styrene monomer may be used, with the sum of the percentages (by weight) being equal to 100%. The acyrlic monomer can be methyl or ethyl(meth)acrylate. The styrene monomer can be styrene or α-methylstyrene.

According to at least one embodiment, the at least one type of particle as disclosed herein is chosen from hollow particles of an expanded copolymer of vinylidene chloride and acrylonitrile, and hollow particles of an expanded copolymer of vinylidene chloride, acrylonitrile and methyl methacrylate. These particles may be dry or hydrated.

According to at least one embodiment, the mass per unit volume of these particles can range from 15 to 200 kg/m$^3$, such as from 40 to 120 kg/m$^3$, and further such as from 60 to 80 kg/m$^3$.

The at least one type of particle as disclosed herein can be chosen from, for example, microspheres of expanded terpolymer of vinylidene chloride, acrylonitrile and methyl methacrylate, sold under the brand name EXPANCEL by the company Nobel Casco and such as under the references 551 DE 12 (particle size D(0.5) of about 12 μm and mass per unit volume of about 40 kg/m$^3$), 551 DE 20 (particle size D(0.5) of about 15 to 25 μm and mass per unit volume of about 60 kg/m$^3$), 551 DE 50 (particle size D(0.5) of about 40 μm), 461 DE 50 and 642 WE 50 of about 50 μm of particle size D(0.5), 551 DE 80 (particle size D(0.5) of about 50 to 80 μm). It is also possible to use particles of this same expanded terpolymer with a particle size D(0.5) of about 18 μm and a mass per unit volume of about 60 to 80 kg/m$^3$ (EXPANCEL EL23) or with a particle size D(0.5) of about 34 μm and a mass per unit volume of about 20 kg/m$^3$. Mention may also be made, for example, of the EXPANCEL particles 551 DE 40 d42 (particle size D(0.5) of about 30 to 50 μm and a mass per unit volume of about 42 kg/m$^3$), 551 DE 80 d42 (particle size D(0.5) of about 50 to 80 μm and a mass per unit volume of about 42 kg/m$^3$), 461 DE 20 d70 (particle size D(0.5) of about 15 to 25 μm and a mass per unit volume of about 70 kg/m$^3$), 461 DE 40 d25 (particle size D(0.5) of about 35 to 55 μm and a mass per unit volume of about 25 kg/m$^3$), 461 DE 40 d60 (particle size D(0.5) of about 20 to 40 μm and a mass per unit volume of about 60 kg/m$^3$), 461 DET 40 d25 (particle size D(0.5) of about 35 to 55 μm and a mass per unit volume of about 25 kg/m$^3$), 051 DE 40 d60 (particle size D(0.5) of about 20 to 40 μm and a mass per unit volume of about 60 kg/m$^3$), 091 DE 40 d30 (particle size D(0.5) of about 35 to 55 μm and a mass per unit volume of about 30 kg/m$^3$), 091 DE 80 d30 (particle size D(0.5) of about 60 to 90 μm and a mass per unit volume of about 30 kg/m$^3$). It is also possible to use particles of a copolymer of vinylidene chloride and acrylonitrile, or a copolymer of vinylidene chloride, acrylonitrile and methyl methacrylate, in unexpanded form, for instance those sold under the brand name EXPANCEL with the reference 551 DU 10 (particle size D(0.5) of about 10 μm) or 461 DU 15 (particle size D(0.5) of about 15 μm).

Among the microporous microspheres that may be used in the composition as disclosed herein, exemplary mention may be made of those sold by Dow Corning under the name POLYTRAP which are formed from lauryl methacrylate/ethylene glycol dimethacrylate copolymers; or those sold by SEPPIC under the name MICROPEARL.

Among other polymeric hollow particles that may be used in the composition, exemplary mention may also be made of polymers and copolymers obtained from itaconic, citraconic, maleic or fumaric esters or acids, and vinyl acetate or lactate (see in this respect document JP-A-2 112 304).

According to at least one embodiment, the at least one organic structuring agent is in the form of hollow particles.

The at least one organic structuring agent can be present in the compositon in a total amount ranging from 1% to 10%, such as from 2% to 6%, further such as from 2.5% to 5% and even further such as from 3% to 4% by weight relative to the total weight of the cosmetic composition.

The composition also comprises at least one mixture of two types of absorbents, at least one type of which is modified starch, and at least one type of which is wood meal.

The term "absorbent" means any compound capable of rapidly trapping a large amount of water. The organic absorbent can be a hydrophilic or amphiphilic compound.

As disclosed herein, the term "absorbent" means any compound having a static water absorption capacity, at room temperature (25° C.) of greater than or equal to three times its own weight.

For example, absorbents can be chosen from compounds with a static water absorption capacity of greater than or equal to five times their own weight and such as greater than or equal to 15 times their own weight.

The test for measuring the static water absorption capacity is described without limiting the scope thereof in the latter experimental section of this disclosure.

This absorbent may make it possible to obtain a composition in solid, such as deformable, form that may break down easily with the aid of a diluent that can be cold or hot water, but may also be water comprising at least one cosmetically acceptable polar solvent, such as an alcohol comprising 2 to 20 carbon atoms (isopropanol or ethanol for example), propylene glycol, or water comprising at least one surfactant. It is also possible to use more complex aqueous media.

As disclosed herein, the term "modified starch" means starches that are chemically modified via at least one of the reactions chosen from pregelatinization, oxidation, crosslinking, esterification, and heat treatment.

The at least one modified starch may originate from a plant source such as cereals, tubers, roots, legumes and fruit. Hydrolysates thereof may also be used. Thus, for example, the at least one modified starch may originate from a plant source chosen from corn, pea, potato, sweet potato, banana, barley, wheat, rice, oat, sago, tapioca and sorghum.

The at least one modified starch can be chosen from potato starches.

The at least one modified starch can be in the form of a white powder, which can be insoluble in cold water, whose mean particle size may range from 3 to 100 microns.

As an example, the modification reactions may be performed in the following manner:
pregelatinization by splitting the starch granules (for example drying and cooking in a drying drum);
oxidation with strong oxidizing agents leading to the introduction of carboxyl groups into the starch molecule and to depolymerization of the starch molecule (for example by treating an aqueous starch solution with sodium hypochlorite);
crosslinking with functional agents capable of reacting with the hydroxyl groups of the starch molecules, which will thus bind together (for example with glyceryl and/or phosphate groups);
esterification in alkaline medium for the grafting of functional groups, such as C1-C6 acyl(acetyl), C1-C6 hydroxyalkyl(hydroxyethyl, hydroxypropyl), carboxymethyl or octenylsuccinic. Mention may be made, for example, of starches modified with sodium carboxymethyl.

Monostarch phosphates (of the type Am—O—PO—(OX)2), distarch phosphates (of the type Am—O—PO—(OX)—O—Am) or even tristarch phosphates (of the type Am—O—PO—(O—Am)2) or mixtures thereof, may, for example, be obtained by crosslinking with phosphorus compounds.

X denotes alkali metals (for example sodium or potassium), alkaline-earth metals (for example calcium or magnesium), ammonium salts, amine salts such as those of monoethanolamine, diethanolamine, triethanolamine or 3-amino-1,2-propanediol, and ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Among the at least one modified starch that may be used, exemplary mention may be made of quaternized pregelatinized potato starches, pregelatinized corn starches, crosslinked potato carboxymethyl starches, pregelatinized and optionally hydroxypropylated cassava distarch phosphates, and pregelatinized and optionally acetylated potato distarch phosphates.

Among the commercially available products that may be mentioned are the products sold by Avebe under the names PREGEL or PRIMOGEL, or those sold by National Starch under the name STRUCTURE ZEA.

It is also possible to use at least one amphoteric starch, comprising at least one anionic group and at least one cationic group. The anionic and cationic groups may be attached to the same reactive site of the starch molecule or to different reactive sites; they can be for example attached to the same reactive site. The anionic groups may be of carboxylic, phosphate or sulfate type, for example of carboxylic type. The cationic groups may be of primary, secondary, tertiary or quaternary amine type.

The at least one amphoteric starch can be chosen from the compounds of formulae (I)-(IV):

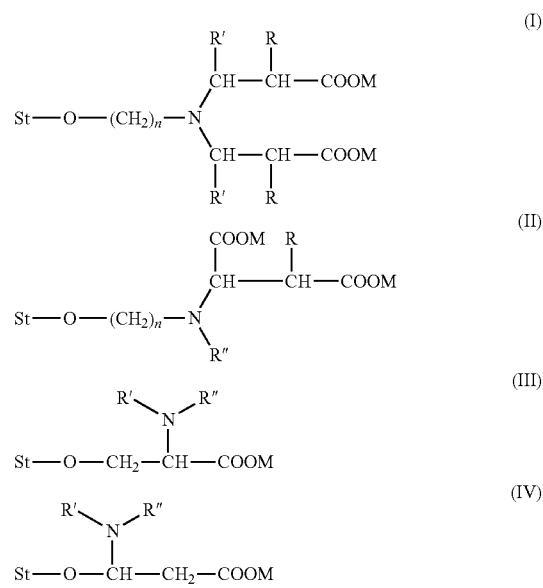

in which formulae:
St-O represents a starch molecule,
R, which may be identical or different, represents a hydrogen atom or a methyl radical,
R', which may be identical or different, represents a hydrogen atom, a methyl radical or —COOH,
n is an integer equal to 2 or 3,
M, which may be identical or different, represents a hydrogen atom, an alkali metal or alkaline-earth metal such as Na, K or Li, NH$_4$, a quaternary ammonium or an organic amine,
R" represents a hydrogen atom or an alkyl radical comprising from 1 to 18 carbon atoms.

These compounds are for example described in U.S. Pat. Nos. 5,455,340 and 4,017,460.

According to at least one embodiment, the starches of formula (I) or (II) are used. For example, starches modified with 2-chloroethylaminodipropionic acid, i.e. the starches of the formula (I) or (II) in which R, R', R" and M represent a hydrogen atom and n is equal to 2, can be used. Mention may be made, for example, of the potato starch modified with 2-chloroethylaminodipropionic acid neutralized with sodium hydroxide, sold under the reference STRUCTURE SOLANACE by the company National Starch.

In at least one embodiment, the at least one wood meal can be chosen from spruce meal or beech meal, such as spruce meal.

The mean particle size of the wood meals is for example less than 250 μm.

Such products are for example sold by Société Parisienne des Sciures under the name T140 (spruce meal) or H160/0 (beech meal).

Thus, for example, the at least one modified starch is modified potato starch and the at least one wood meal is spruce meal.

The at least one modified starch and the at least one wood meal can be present in the composition in a total combined amount ranging from 3% to 50%, such as from 5% to 35% and further such as from 10% to 20% by weight relative to the total weight of the composition.

For example, the at least one modified starch can be present in the composition in a total amount ranging from 3% to 25% and such as from 4% to 15% by weight relative to the total weight of the composition.

For example, the at least one wood meal can be present in a total amount ranging from 1% to 25% and such as from 1.5% to 15% by weight relative to the total weight of the composition.

Thus, according to at least one embodiment, the composition as disclosed herein comprises 4% to 12% by weight of modified potato starch and 2% to 12% by weight of spruce meal relative to the total weight of the composition.

Besides the at least one organic structuring agent and the at least two absorbents, the composition as disclosed herein comprises at least one surfactant.

The at least one surfactant, which can be anhydrous, i.e. comprising no water or comprising water in an amount of less than 5% by weight, may be chosen from cationic, anionic, nonionic and amphoteric surfactants.

Among the anionic surfactants that may be used in the compositions as disclosed herein, non-limiting mention may be made for example of salts, such as alkali metal salts, and further such as sodium salts, ammonium salts, amine salts, amino alcohol salts or magnesium salts of the following compounds: alkyl sulfates, alkyl ether sulfates, alkyl amidoether sulfates, monoglyceride sulfates, alkylglyceryl sulfonates, alkyl sulfonates, alkyl phosphates, alkylamide sulfonates, alkylaryl sulfonates, α-olefin sulfonates, paraffin sulfonates, alkylsulfosuccinates, alkyl ether sulfosuccinates, alkylamide sulfosuccinates, alkyl sulfosuccinamates, alkyl sulfoacetates, alkyl ether phosphates, acyl isethionates, N-acyltaurates, N-acylamino acids such as N-acylsarcosinates and N-acylglutamates. As anionic surfactants that may be used in the compositions as disclosed herein, non-limiting mention may also be made of fatty acid salts such as salts of undecenylic acid, oleic acid, ricinoleic acid, palmitic acid and stearic acid, coconut oil acid or hydrogenated coconut oil acid and acylhydroxy acids such as acyl lactylates. It is also possible to use weakly anionic surfactants such as alkyl D-galactoside uronic acids and salts thereof, and also polyoxyalkylenated alkyl ether alkylamido ether carboxylic acids or salts thereof, the alkyl or acyl radical of these various compounds for example comprising from 8 to 22 carbon atoms, and anionic derivatives of $(C_8-C_{22})$alkyl polyglycosides (sulfate, sulfosuccinate, phosphate, isethionate, ether carboxylate, carbonate).

Among the amphoteric surfactants that may for example be mentioned are secondary or tertiary aliphatic amine derivatives, in which the aliphatic radical is a linear or branched chain comprising 8 to 22 carbon atoms and comprising at least one hydrosolubilizing anionic group, for instance a carboxylate, sulfonate, sulfate, phosphate or phosphonate group. Among the surfactants of amphoteric or zwitterionic type, exemplary mention may also be made of sulfobetaines, alkylamidoalkylbetaines, alkylamidoalkylsulfobetaines and imidazolium derivatives such as those of amphocarboxyglycinate or of amphocarboxypropionate.

Among the nonionic surfactants in the compositions as disclosed herein, exemplary mention may be made of polyethoxylated, polypropoxylated or polyglycerolated derivatives of alcohols, of α-diols or of alkylphenols or of fatty acids, with a fatty chain comprising from 8 to 28 carbon atoms, the number of ethylene oxide or propylene oxide groups possibly ranging from 2 to 50 and the number of glycerol groups for example ranging from 2 to 30. Mention may also for example be made of copolymers of ethylene oxide and propylene oxide, condensates of ethylene oxide and propylene oxide with fatty alcohols, polyethoxylated fatty amides for example comprising from 2 to 30 mol of ethylene oxide, polyglycerolated fatty amides comprising on average 1 to 5 glycerol groups, polyglycerolated diglycolamides, optionally oxyethylenated fatty acid esters of sorbitan, fatty acid esters of sucrose, polyoxyalkylenated fatty acid esters, optionally oxyalkylenated alkylpolyglycosides, alkylglucoside esters, N-alkylglucamine and N-acylmethylglucamine derivatives, aldobionamides and amine oxides.

Non-limiting cationic surfactants that may be mentioned, include: primary, secondary or tertiary fatty amine salts, optionally polyoxyalkylenated; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives.

Cationic surfactants that may also be used are quaternary ammonium salts comprising at least one ester function, such as those of formula (V):

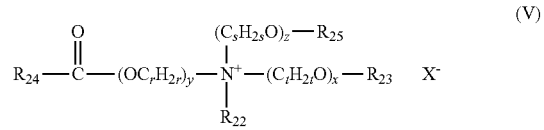

in which:

$R_{22}$ is chosen from $C_1-C_6$ alkyl radicals, $C_1-C_6$ hydroxyalkyl, and dihydroxyalkyl radicals;

$R_{23}$ is chosen from:
the radical

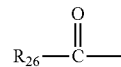

linear and branched, saturated and unsaturated $C_1-C_{22}$ hydrocarbon-based radicals $R_{27}$, and
a hydrogen atom, $R_{25}$ is chosen from:
the radical

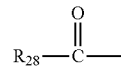

linear and branched, saturated and unsaturated $C_1-C_6$ hydrocarbon-based radicals $R_{29}$, and
a hydrogen atom, $R_{24}$, $R_{26}$ and $R_{28}$, which may be identical or different, are chosen from linear and branched, saturated and unsaturated $C_7-C_{21}$ hydrocarbon-based radicals;

r, s and t, which may be identical or different, are integers ranging from 2 to 6;

y is an integer ranging from 1 to 10;

x and z, which may be identical or different, are integers ranging from 0 to 10;

$X^-$ is a simple or complex, organic or inorganic anion;

with the proviso that the sum x+y+z ranges from 1 to 15, that when x is 0, then $R_{23}$ represents $R_{27}$ and that when z is 0, then $R_{25}$ represents $R_{29}$.

The alkyl radicals $R_{22}$ may be linear or branched, and for example may be linear.

According to at least one embodiment, $R_{22}$ represents a methyl, ethyl, hydroxyethyl or dihydroxypropyl radical, such as a methyl or ethyl radical.

As an example, the sum x+y+z may range from 1 to 10.

When $R_{23}$ is a hydrocarbon-based radical $R_{27}$, it may be long and comprise from 12 to 22 carbon atoms, or short and comprise from 1 to 3 carbon atoms.

When $R_{25}$ is a hydrocarbon-based radical $R_{29}$, it can comprise 1 to 3 carbon atoms.

For example, $R_{24}$, $R_{26}$ and $R_{28}$, which may be identical or different, are chosen from linear and branched, saturated and unsaturated $C_{11}$-$C_{21}$ hydrocarbon-based radicals and for further example from linear and branched, saturated and unsaturated $C_{11}$-$C_{21}$ alkyl and alkenyl radicals.

For example, in at least one embodiment, x and z, which may be identical or different, are 0 or 1.

In at least one embodiment, y is equal to 1.

For example, r, s and t, which may be identical or different, are 2 or 3, and for further example are equal to 2.

The anion is for example a halide (chloride, bromide or iodide) or an alkyl sulfate, for further example a methyl sulfate. However, methanesulfonate, phosphate, nitrate, tosylate, an anion derived from an organic acid such as acetate or lactate, or any other anion that is compatible with the ammonium comprising an ester function, may be used.

According to at least one embodiment, the anion $X^-$ is chloride or methyl sulfate.

Among the ammonium salts of formula (V), the compounds that may be used are those in which:
$R_{22}$ represents a methyl or ethyl radical,
x and y are equal to 1;
z is equal to 0 or 1;
r, s and t are equal to 2;
$R_{23}$ is chosen form:
the radical

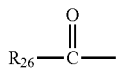

methyl, ethyl and $C_{14}$-$C_{22}$ hydrocarbon-based radicals; and
a hydrogen atom;
$R_{25}$ is chosen from:
the radical

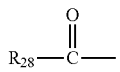

and
a hydrogen atom;
$R_{24}$, $R_{26}$ and $R_{28}$, which may be identical or different, are chosen from linear and branched, saturated and unsaturated $C_{13}$-$C_{17}$ hydrocarbon-based radicals, and such as from linear and branched, saturated and unsaturated $C_{13}$-$C_{17}$ alkyl and alkenyl radicals.

According to at least one embodiment, the hydrocarbon-based radicals are linear.

Non-limiting examples that may be mentioned include the compounds of formula (V) such as the salts (such as chloride or methyl sulfate) of diacyloxyethyldimethylammonium, of diacyloxyethylhydroxyethylmethylammonium, of monoacyloxyethyldihydroxyethylmethylammonium, of triacyloxyethylmethylammonium or of monoacyloxyethylhydroxyethyldimethylammonium and mixtures thereof. The acyl radicals may comprise 14 to 18 carbon atoms and can be derived from a plant oil such as palm oil or sunflower oil. When the compound comprises several acyl radicals, these radicals may be identical or different. Mention may be made for example of distearoylethylhydroxyethylammonium methosulfate.

These products are obtained, for example, by direct esterification of triethanolamine, triisopropanolamine, an alkyldiethanolamine or an alkyl diisopropanolamine, which are optionally oxyalkylenated, with fatty acids or with mixtures of fatty acids of plant or animal origin, or by transesterification of the methyl esters thereof. This esterification can be followed by quaternization using an alkylating agent such as an alkyl halide (such as a methyl or ethyl halide), a dialkyl sulfate (such as methyl or ethyl sulfate), methyl methanesulfonate, methyl para-toluenesulfonate, or glycol or glycerol chlorohydrin.

The composition as disclosed herein may comprise a mixture of mono-, di- and triester salts of quaternary ammonium with diester salts as the major component by weight.

Examples of mixtures of ammonium salts that may be used include the mixture comprising 15% to 30% by weight of acyloxyethyldihydroxyethylmethylammonium methyl sulfate, 45% to 60% diacyloxyethylhydroxyethylmethylammonium methyl sulfate and 15% to 30% triacyloxyethylmethylammonium methyl sulfate, the acyl radicals comprising from 14 to 18 carbon atoms and being derived from optionally partially hydrogenated palm oil.

Ammonium salts comprising at least one ester function, such as those described in U.S. Pat. Nos. 4,874,554 and 4,137,180, may also be used.

As non-limiting examples of the at least one surfactant that are suitable for producing the compositions as disclosed herein, mention may be made of REWOPOL SB F 12 P, the active agent of which is sodium lauryl sulfosuccinate, TEXAPON Z 95 P, the active agent of which is sodium lauryl sulfate, GENAMIN KDMP, the active agent of which is behenyltrimethylammonium chloride, DEHYQUAT F 75, the active agent of which is dicetearoylethylhydroxyethylmethylammonium methosulfate, and TWEEN 21, the active agent of which is sorbitan monolaurate comprising 4 mol of ethylene oxide.

For example, the at least one surfactant can be anhydrous and in powder form. They may have a mean particle size ranging from 5 to 50 μm and such as from 10 to 20 μm.

The at least one surfactant can be present in the composition in a total amount ranging from 1% to 40%, such as from 2% to 20% and further such as from 4% to 20% by weight relative to the total weight of the composition.

When the composition is a shampoo, it may comprise at least one anionic surfactant.

When the composition is a hair conditioner, it may comprise at least one cationic surfactant in a total amount ranging from 1% to 10% and such as from 2% to 5% by weight relative to the total weight of the composition.

The composition as disclosed herein also comprises at least one anhydrous liquid phase.

The at least one anhydrous liquid phase may comprise at least one compound chosen from monoalcohols, polyols and fatty substances.

The at least one monoalcohol may be chosen from ethanol and isopropanol.

The at least one polyol may be chosen from glycerol and glycol, for instance propylene glycol, hexylene glycol and polyethylene glycol.

The at least one fatty substance may be chosen from oils, waxes and silicones.

The at least one oil that may be used in the composition as disclosed herein may be chosen from mineral oils, for instance liquid paraffin and liquid petroleum jelly; oils of animal origin such as perhydrosqualene; oils of plant origin such as sweet almond oil, avocado oil, castor oil, olive oil, jojoba oil, sesame oil, groundnut oil, grapeseed oil, rapeseed oil, coconut oil, hazelnut oil, palm oil, apricot kernel oil, beauty-leaf oil, rice bran oil, corn germ oil, wheat germ oil, soybean oil, sunflower oil, safflower oil, passion flower oil, rye oil, shea butter and the liquid fraction thereof; synthetic oils such as fatty esters, for instance butyl and isopropyl myristate, hexadecyl, isopropyl, octyl and isodecyl stearate, decyl oleate, hexyl laurate, propylene glycol dicaprylate, lanolic acid ester derivatives such as isopropyl lanolate and isocetyl lanolate, isoparaffins, acetylglycerides, alcohol and polyalcohol octanoates such as those of glycol and glycerol, alcohol and polyalcohol ricinoleates, and fatty acid triglycerides; silicon oils such as cyclomethicones, volatile and non-volatile polydimethylsiloxanes, and phenyldimethylsiloxanes.

Among the waxes that may be used, exemplary mention may be made of beeswax, lanolin wax and Chinese insect waxes, carnauba wax, candelilla wax, ouricury wax, cork fibre wax, sugarcane wax, Japan wax, hydrogenated jojoba wax, and hydrogenated oils such as hydrogenated sunflower oil, hydrogenated castor oil, hydrogenated coconut oil and hydrogenated lanolin oil; paraffins, microcrystalline waxes, montan waxes and ozokerites; polyethylene waxes, the waxes obtained by Fischer-Tropsch synthesis, waxy copolymers and esters thereof, and silicon waxes such as polyalkoxy- and polyalkylsiloxanes.

The silicones that may be used in the composition as disclosed herein are for example polyorganosiloxanes that may be in the form of aqueous solutions, i.e. dissolved, or optionally in the form of dispersions or microdispersions, or of aqueous emulsions. The polyorganosiloxanes may also be in the form of oils, waxes, resins or gums.

Organopolysiloxanes are described in greater detail in, for example, Walter Noll's *Chemistry and Technology of Silicones* (1968), Academic Press.

The silicones may be volatile or non-volatile.

When they are volatile, the silicones can be chosen from those with a boiling point ranging from 60° C. to 260° C., and further can be chosen from:

(i) cyclic silicones comprising from 3 to 7 and such as from 4 to 5 silicon atoms.

These are, for example, octamethylcyclotetrasiloxane sold for example under the name VOLATILE SILICONE 7207 by Union Carbide or SILBIONE 70045 V 2 by Rhône-Poulenc, decamethylcyclopentasiloxane sold under the name VOLATILE SILICONE 7158 by Union Carbide, and SILBIONE 70045 V 5 by Rhône-Poulenc, and mixtures thereof.

Mention may also for example be made of cyclocopolymers of the dimethylsiloxanes/methylalkylsiloxane type, such as VOLATILE SILICONE FZ 3109 sold by the company Union Carbide, with the chemical structure:

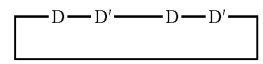

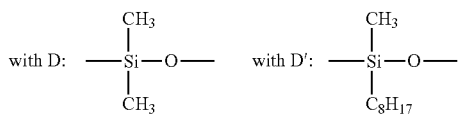

Mention may also for example be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones comprising 2 to 9 silicon atoms and having a viscosity of less than or equal to $5 \times 10^{-6}$ m$^2$/s at 25° C. An example is decamethyltetrasiloxane sold for example under the name SH 200 by the company Toray Silicone. Silicones belonging to this category are also described, for example, in the article published in Cosmetics and Toiletries, Vol. 91, January 1976, pp. 27-32, Todd & Byers "Volatile Silicone Fluids for Cosmetics".

Non-volatile silicones and for example polyalkylsiloxanes, polyarylsiloxanes, polyalkylarylsiloxanes, silicone gums and resins, and polyorganosiloxanes modified with organofunctional groups, and mixtures thereof, can be used.

These additional silicones are for example chosen from polyalkylsiloxanes, among which mention may be made for example of polydimethylsiloxanes comprising trimethylsilyl end groups (Dimethicone according to the CTFA name) having a viscosity of from $5 \times 10^{-6}$ to 2.5 m$^2$/s at 25° C. and such as $1 \times 10^{-5}$ to 1 m$^2$/s. The viscosity of the silicones is measured, for example, at 25° C. according to ASTM standard 445 Appendix C.

Among these polyalkylsiloxanes, mention may be made, in a non-limiting manner, of the following commercial products:

the SILBIONE oils of the 47 and 70 047 series or the MIRASIL oils sold by Rhône-Poulenc, such as, for example, the oil 70 047 V 500 000;

the oils of the MIRASIL series sold by the company Rhône-Poulenc;

the oils of the 200 series from the company Dow Corning, such as, DC200 with a viscosity of 60,000 cSt;

the VISCASIL oils from General Electric and certain oils of the SF series (SF 96, SF 18) from General Electric.

Non-limiting mention may also be made of polydimethylsiloxanes comprising dimethylsilanol end groups (Dimethiconol according to the CTFA name) such as the oils of the 48 series from the company Rhône-Poulenc.

Non-limiting mention may also be made of polydimethylsiloxanes comprising aminoethyl aminopropyl and α,ω-silanol.

In this category of polyalkylsiloxanes, non-limiting mention may also be made of the products sold under the names ABIL WAX 9800 and 9801 by the company Goldschmidt, which are poly(C$_1$-C$_{20}$)alkylsiloxanes.

The polyalkylarylsiloxanes are for example chosen from linear and branched polydimethyl methylphenyl siloxanes and polydimethyl diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:

the SILBIONE oils of the 70 641 series from Rhône-Poulenc;

the oils of the RHODORSIL 70 633 and 763 series from Rhône-Poulenc;

the oil DOW CORNING 556 Cosmetic Grade Fluid from Dow Corning;

the silicones of the PK series from Bayer, such as the product PK20;

the silicones of the series PN and PH from Bayer, such as the products PN1000 and PH1000;

certain oils of the SF series from General Electric, such as SF 1023, SF 1154, SF 1250 and SF 1265.

The silicone gums that may be used in the composition as disclosed herein can be polydiorganosiloxanes having high number-average molecular masses ranging from 200,000 to 1,000,000, used alone or as a mixture in at least one solvent. The at least one solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecanes, or mixtures thereof.

Mention may be made for example of the following products:

polydimethylsiloxane gums,
polydimethylsiloxane/methylvinylsiloxane gums,
polydimethylsiloxane/diphenylsiloxane gums,
polydimethylsiloxane/phenylmethylsiloxane gums,
polydimethylsiloxane/diphenylsiloxane/methylvinylsiloxane gums.

Products that may be used for example are the following mixtures:

mixtures of a polydimethylsiloxane hydroxylated at the end of the chain (known as dimethiconol according to the nomenclature of the CTFA dictionary) and a cyclic polydimethylsiloxane (known as cyclomethicone according to the nomenclature of the CTFA dictionary), such as the product Q2 1401 sold by the company Dow Corning;

mixtures of a polydimethylsiloxane gum and a cyclic silicone, such as the product SF 1214 SILICONE FLUID from the company General Electric, this product being an SF 30 gum corresponding to a dimethicone, having a number-average molecular weight of 500,000, dissolved in the oil SF 1202 SILICONE FLUID corresponding to decamethylcyclopentasiloxane;

mixtures of two PDMSs of different viscosities, and for example of a PDMS gum and a PDMS oil, such as the product SF 1236 from the company General Electric. The product SF 1236 is a mixture of an SE 30 gum defined above, with a viscosity of 20 m²/s, and an SF 96 oil with a viscosity of 5×10⁻⁶ m²/s. This product can comprise 15% SE 30 gum and 85% of an SF 96 oil.

The organopolysiloxane resins that may be used in the composition as disclosed herein can be crosslinked siloxane systems comprising the following units: $R_2SiO_{2/2}$, $R_3SiO_{1/2}$, $RSiO_{3/2}$ and $SiO_{4/2}$ in which R represents a hydrocarbon group comprising 1 to 16 carbon atoms or a phenyl group. Among these products, exemplary mention may be made of the ones in which R represents a $C_1$-$C_4$ lower alkyl radical, such as a methyl, or a phenyl radical.

Among these resins, exemplary mention may be made of the product sold under the name DOW CORNING 593 or those sold under the names SILICONE FLUID SS 4230 and SS 4267 by the company General Electric, which are silicones of dimethyl/trimethyl siloxane structure.

Non-limiting mention may also be made of the trimethyl siloxysilicate type resins sold for example under the names X22-4914, X21-5034 and X21-5037 by the company Shin-Etsu.

The organomodified silicones that may be used in the composition as disclosed herein are silicones as defined above and comprising in their structure at least one organofunctional group attached via a hydrocarbon-based radical.

Among the organomodified silicones, exemplary mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the $(C_{12})$alkylmethicone copolyol sold by the company Dow Corning under the name Q2 5200;

thiol groups, such as the products sold under the names "GP 72 A" and "GP 71" from Genesee;

alkoxylated groups, such as the product sold under the name "SILICONE COPOLYMER F-755" by SWS Silicones and ABIL WAX® 2428, 2434 and 2440 by the company Goldschmidt;

hydroxylated groups, such as the polyorganosiloxanes comprising a hydroxyalkyl function, for example, described in French patent application FR-A-85/16334;

acyloxyalkyl groups, such as, for example, the polyorganosiloxanes described in U.S. Pat. No. 4,957,732;

anionic groups of the carboxylic acid type, such as, for example, in the products described in patent EP 186 507 from the company Chisso Corporation, or of the alkyl-carboxylic type, such as those present in the product X-22-3701E from the company Shin-Etsu; 2-hydroxyalkyl sulfonate; 2-hydroxyalkyl thiosulfate such as the products sold by the company Goldschmidt under the names "ABIL® S201" and "ABIL® S255";

hydroxyacylamino groups, such as the polyorganosiloxanes described in patent application EP 342 834. Mention may be made, for example, of the product Q2-8413 from the company Dow Corning.

Among the organomodified silicones, mention may also be made of amino silicones.

The term "amino silicone" means any silicone comprising at least one primary, secondary or tertiary amine function or at least one quaternary ammonium group.

The amino silicones that may be used in the cosmetic composition as disclosed herein are chosen from:

(a) the compounds corresponding to formula (VI) below:

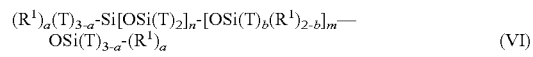

$$(R^1)_a(T)_{3-a}\text{-}Si[OSi(T)_2]_n\text{-}[OSi(T)_b(R^1)_{2-b}]_m\text{-}OSi(T)_{3-a}\text{-}(R^1)_a \quad (VI)$$

in which:

T is a hydrogen atom or a phenyl, hydroxyl (—OH) or $C_1$-$C_8$ alkyl radical, such as methyl, or a $C_1$-$C_8$ alkoxy, such as methoxy, a denotes the number 0 or an integer ranging from 1 to 3, and such as 0, b denotes 0 or 1, and such as 1, m and n are numbers such that the sum (n+m) can range for example from 1 to 2000 and for further example from 50 to 150, n possibly denoting a number from 0 to 1999 and such as from 49 to 149, and m possibly denoting a number from 1 to 2000 and such as from 1 to 10;

$R^1$ is a monovalent radical of formula —$C_qH_{2q}L$ in which q is a number ranging from 2 to 8 and L is an optionally quaternized amino group chosen from the following groups:

—N($R^2$)—$CH_2$—$CH_2$—N($R^2$)$_2$;
—N($R^2$)$_2$;
—$N^+$($R^2$)$_3Q^-$;
—$N^+$($R^2$)(H)$_2Q^-$;
—$N^+$($R^2$)$_2HQ^-$;
—N($R^2$)—$CH_2$—$CH_2$—$N^+$($R^2$)(H)$_2Q^-$, in which $R^2$ can represent a hydrogen atom, a phenyl, a benzyl or a saturated monovalent hydrocarbon-based radical, for example a $C_1$-$C_{20}$ alkyl radical, and $Q^-$ represents a halide ion such as, for example, fluoride, chloride, bromide or iodide.

For example, the amino silicones corresponding to the formula (VI) can be chosen from the compounds chosen from those of formula (VII):

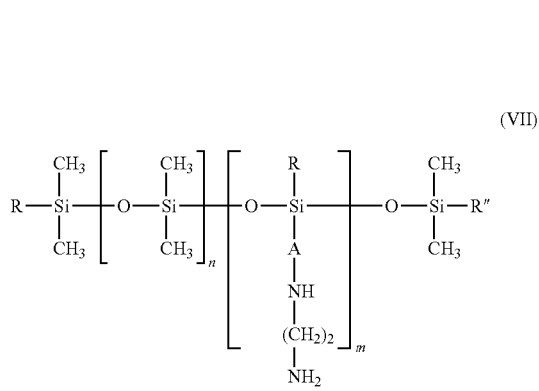

(VII)

in which R, R' and R", which may be identical or different, represent a $C_1$-$C_4$ alkyl radical, such as $CH_3$; a $C_1$-$C_4$ alkoxy radical, such as methoxy; or OH; A represents a linear or branched, $C_3$-$C_8$ and for example $C_3$-$C_6$ alkylene radical; m and n are integers dependent on the molecular weight and whose sum ranges from 1 to 2000.

According to at least one embodiment, R, R' and R", which may be identical or different, represent a $C_1$-$C_4$ alkyl or hydroxyl radical, A represents a $C_3$ alkylene radical and m and n are such that the weight-average molecular mass of the compound ranges from 5,000 to 500,000. Compounds of this type are referred to in the CTFA dictionary as "amodimethicones".

According to at least one embodiment, R, R' and R", which may be identical or different, represent a $C_1$-$C_4$ alkoxy or hydroxyl radical, at least one of the radicals R or R" is an alkoxy radical and A represents a $C_3$ alkylene radical. The hydroxyl/alkoxy molar ratio can range from 0.2:1 to 0.4:1, such as equal to 0.3:1. Moreover, m and n are such that the weight-average molecular mass of the compound ranges from 2,000 to 1,000,000. For further example, n ranges from 0 to 999 and m ranges from 1 to 1,000, the sum of n and m ranges from 1 to 1,000.

Among this category of compounds, mention may be made, inter alia, of the product BELSIL® ADM 652 sold by Wacker.

According to at least one embodiment, R and R", which are different, represent a $C_1$-$C_4$ alkoxy or hydroxyl radical, at least one of the radicals R or R" is an alkoxy radical, R' represents a methyl radical and A represents a $C_3$ alkylene radical. The hydroxyl/alkoxy molar ratio can range from 1:0.8 to 1:1.1 and for example, in at least one embodiment, is equal to 1:0.95. Moreover, m and n are such that the weight-average molecular mass of the compound ranges from 2,000 to 200,000. For further example, n ranges from 0 to 999 and m ranges from 1 to 1,000, and the sum of n and m ranges from 1 to 1,000.

For example, mention may be made of the product FLUID WR® 1300 sold by the company Wacker.

It should be noted that the molecular mass of these silicones can be determined by gel permeation chromatography (ambient temperature, polystyrene standard; μ styragem columns; eluent THF; flow rate 1 mm/m; 200 μl of a solution containing 0.5% by weight of silicone are injected into THF and detection is performed by refractometry and UV-metry).

One compound corresponding to formula (VI) is, for example, the polymer known in the CTFA dictionary as "trimethylsilyl amodimethicone," corresponding to formula (VIII) below:

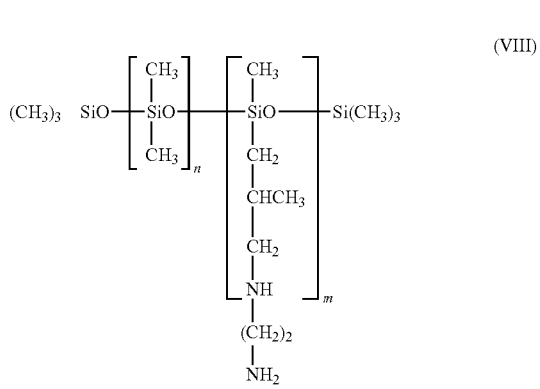

(VIII)

in which n and m have the meanings given above in accordance with formula (VI).

Such compounds are described, for example, in patent application EP95238; a compound of formula (VIII) is sold, for example, under the name Q2-8220 by the company OSI.

(b) the compounds corresponding to formula (IX) below:

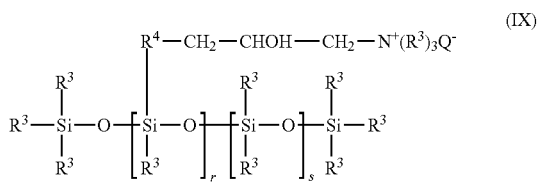

(IX)

in which:

$R^3$ represents a monovalent $C_1$-$C_{18}$ hydrocarbon-based radical, such as a $C_1$-$C_{18}$ alkyl or $C_2$-$C_{18}$ alkenyl radical, for example methyl;

$R^4$ represents a divalent hydrocarbon-based radical, such as a $C_1$-$C_{18}$ alkylene radical or a divalent $C_1$-$C_{18}$, and for example $C_1$-$C_8$, alkyleneoxy radical;

$Q^-$ is a halide ion, such as chloride;

r represents an average statistical value ranging from 2 to 20 and for example from 2 to 8;

s represents an average statistical value ranging from 20 to 200 and for example from 20 to 50.

Such compounds are described for example in U.S. Pat. No. 4,185,087.

One example of the compounds falling within this class is the product sold by the company Union Carbide under the name UCAR SILICONE ALE 56.

(c) the quaternary ammonium silicones of formula (X):

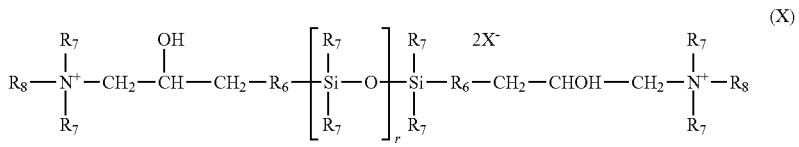

in which:

$R_7$, which may be identical or different, represent a monovalent hydrocarbon-based radical comprising from 1 to 18 carbon atoms, such as a $C_1$-$C_{18}$ alkyl radical, a $C_2$-$C_{18}$ alkenyl radical or a ring comprising 5 or 6 carbon atoms, for example methyl;

$R_6$ represents a divalent hydrocarbon-based radical, such as a $C_1$-$C_{18}$ alkylene radical or a divalent $C_1$-$C_{18}$, for example $C_1$-$C_8$, alkyleneoxy radical linked to the Si via an Si—C bond;

$R_8$, which may be identical or different, represent a hydrogen atom, a monovalent hydrocarbon-based radical comprising from 1 to 18 carbon atoms, such as a $C_1$-$C_{18}$ alkyl radical, a $C_2$-$C_{18}$ alkenyl radical or a radical —$R_6$—NHCOR$_7$ in which $R_6$ and $R_7$ are defined as above;

$X^-$ is an anion such as a halide ion, for example chloride, or an organic acid salt (acetate, etc.);

r represents a mean statistical value ranging from 2 to 200 and such as from 5 to 100.

These silicones are described, for example, in patent application EP-A 0 530 974.

(d) the amino silicones of formula (XI):

$$\underset{\substack{|\\(C_nH_{2n})\\|\\NH\\|\\(C_mH_{2m})\\|\\NH_2}}{Si}\left[O\left[\begin{array}{c}R_1\\|\\Si-O\\|\\R_2\end{array}\right]_x\begin{array}{c}R_3\\|\\Si-R_5\\|\\R_3\end{array}\right]_3$$ (XI)

in which:
$R_1$, $R_2$, $R_3$ and $R_4$, which may be identical or different, represent a $C_1$-$C_4$ alkyl radical or a phenyl group,
$R_5$ represents a $C_1$-$C_4$ alkyl radical or a hydroxyl group,
n is an integer ranging from 1 to 5,
m is an integer ranging from 1 to 5, and
in which x is chosen such that the amine number ranges from 0.01 and 1 meq./g.

According to at least one embodiment, the silicones are polydimethylsiloxanes, dimethicones and/or amodimethicones.

According to at least one embodiment, at least one of the above three types of silicones is used together with at least one cationic and/or nonionic surfactant.

By way of example, mention may be made of the product sold under the name CATIONIC EMULSION DC 939 by the company Dow Corning, which comprises, besides amodimethicone, a cationic surfactant which is trimethylcetylammonium chloride and a nonionic surfactant of formula: $C_{13}H_{27}$—$(OC_2H_4)_{12}$—OH, known under the CTFA name TRIDECETH-12.

Another commercial product that may be used can be the product sold under the name DOW CORNING Q2 7224 by the company Dow Corning, comprising, in combination, the trimethylsilyl amodimethicone of formula (VIII) described above, a nonionic surfactant of formula: $C_8H_{17}$—$C_6H_4$—$(OCH_2CH_2)_{40}$—OH, known under the CTFA name OCTOXYNOL-40, a second nonionic surfactant of formula: $C_{12}H_{25}$—$(OCH_2$—$CH_2)_6$—OH, known under the CTFA name ISOLAURETH-6, and propylene glycol.

The at least one silicone can be present in the composition in a total amount ranging from 0.1% to 20% and such as from 0.1% to 10% by weight relative to the total weight of the composition.

The at least one anhydrous liquid phase can be present in the composition in a total amount of at least 50% and such as ranging from 50% to 95% by weight relative to the total weight of the composition.

The composition as disclosed herein may also comprise at least one additive that is suitable for cosmetic compositions.

For example, it may comprise at least one additive chosen from cationic polymers, fillers, styling agents, heating agents, cosmetic and dermatological active agents, fragrances, UV-screening agents, preserving agents, pH regulators, viscosity regulators, sequestrants, free-radical scavengers, moisturizers, reducing agents or antioxidants, oxidizing agents, dyes, conditioning agents and vitamins.

Among the fillers, exemplary mention may be made of scrubbing particles, decaking aids and agents for reducing the firmness of the composition.

The term "heating agent" means an agent that is capable of giving off heat, during the hydratation of the composition. This agent can be chosen from polyols comprising at least two hydroxyl groups and at least three carbon atoms, such as, glycerol, diglycerol, propylene glycol, butylene glycol, a polyethylene glycol with a molecular weight of less than 600, for instance PEG 400 sold by the company BASF under the name LUTROL E400, sugars such as sorbitol, and mixtures thereof. This type of agent has the feature of reacting with water in an exothermic process. In order for this exothermic process to take place during application, it is desirable for the composition to be free of water.

As examples of cosmetic or dermatological active agents that may be used in the composition as disclosed herein, mention may be made of antibacterial or antifungal agents such as octopirox and triclosan, keratolytic agents such as salicylic acid, essential oils, lipophilic vitamins, antidandruff agents and hair-loss counteractants.

The composition as disclosed herein may be a shampoo, pre-shampoo, hair conditioning, hair shaping, permanent-waving or relaxing, dyeing or bleaching composition, a hair conditioning composition or a foaming composition for the skin (body and/or face).

The composition as disclosed herein is for example rinsed off.

The composition as disclosed herein may be in the form of a wand, a pencil, a stick, a cake or even a paste, and may itself constitute a new type of cosmetic or pharmaceutical product.

The composition as disclosed herein may be in a deformable solid form.

The term "deformable" means that the composition is in a malleable, dry, solid form, resembling marshmallow (see, for example, document U.S. Pat. No. 3,682,659 for the consistency of marshmallow).

The composition as disclosed herein can be applied to wet keratin materials. However, it may also be used on dry keratin materials with addition of a fraction of water after applying the composition.

Provided herein also is a method for cleansing and/or conditioning keratin materials comprising applying at least one of the anhydrous cosmetic compositions as disclosed herein to the keratin materials (skin and/or hair).

The composition as disclosed herein may be prepared by any means known to those skilled in the art, such as by simple mixing of the various constituents and moulding in a suitable mould. It may also be by mixing followed by blending and extrusion in an extruder, for example a twin-screw extruder, further for example a twin-screw extruder such as those described in patents EP 605 284 or FR 2 715 306, and in which the two screws rotate in the same direction.

The extruded mass can leave the extrusion die in the form of rods whose diameter can be given by the die used, which may then be cut up and formed, for example into a wand or a solid cake. Needless to say, other forms may be produced by selecting suitable dies and devices for forming the final products that are adapted to the desired form.

The extruded mass may also be dehydrated and/or ground and/or compacted after production.

The extrusion process may be performed at elevated temperature, at room temperature or in the presence of a cooling system. For example, the entire extrusion process is performed at room temperature, at about 20-25° C., or under cold conditions, which allows the use of heat-sensitive starting materials, such as vitamins or volatile oils.

Moreover, this makes it possible to introduce heat-sensitive starting materials into any zone of the extruder (at the top, in the middle or at the end) since no heat-mediated deterioration needs to be feared. This can be beneficial for the introduction of structuring agents of the type such as EXPANCEL.

It is also possible to perform part of the extrusion under inert gas (for example nitrogen), which may be beneficial when oxidazable products are used.

Since the extrusion can be performed at room temperature, the matrix forming the composition may not be a matrix of an expanded network.

The following examples serve to illustrate the disclosure without limiting the scope thereof.

EXAMPLES

Test for Measuring the Static Water Absorption Capacity x grams of the test compound are placed in a beaker at room temperature; 3x grams of water are added. The whole is left to stand, without stirring, for 1 minute.

If no free water remains (supernatant water) after the minute, the compound may be considered as an absorbent within the scope of the disclosure.

Example 1

A washing foaming composition according to the present disclosure was formulated, the formulation of which was as follows (on a weight basis relative to the total weight of the composition):

| | |
|---|---|
| hollow microspheres of vinylidene chloride/acrylonitrile/methyl methacrylate copolymer expanded with isobutane (EXPANCEL 551 DE 40 d42 from the company Expancel): | 2.55% |
| 96/4 mixture of sodium salt of potato carboxymethyl starch and of ethanol (PRIMOGEL from the company DMV International): | 5.95% |
| spruce meal (wood meal F140 from the company SPPS): | 11.9% |
| propylene glycol: | 20.4% |
| glycerol: | 40.8% |
| sodium lauryl sulfate: | 17.85% |

Example 2

A hair conditioning composition according to the present disclosure was formulated, the formulation of which was as follows (on a weight basis relative to the total weight of the composition):

| | |
|---|---|
| hollow microspheres of vinylidene chloride/acrylonitrile/methyl methacrylate copolymer expanded with isobutane (EXPANCEL 551 DE 40 d42 from the company Expancel): | 3.8% |
| 96/4 mixture of sodium salt of potato carboxymethyl starch and of ethanol (PRIMOGEL from the company DMV International): | 12.3% |
| spruce meal (wood meal F140 from the company SPPS): | 5.3% |
| propylene glycol: | 73% |
| behenyltrimethylammonium chloride (GENAMIN KDMP from Clariant): | 3.2% |
| cetylstearyl alcohol: | 1.6% |
| myristyle/cetyl/stearyl myristate/palmitate/stearate mixture: | 0.8% |

Example 3

A hair conditioning composition according to the present disclosure was formulated, the formulation of which was as follows (on a weight basis relative to the total weight of the composition):

| | |
|---|---|
| hollow microspheres of vinylidene chloride/acrylonitrile/methyl methacrylate copolymer expanded with isobutane (EXPANCEL 551 DE 40 d42 from the company Expancel): | 6.4% |
| 96/4 mixture of sodium salt of potato carboxymethyl starch and of ethanol (PRIMOGEL from the company DMV International): | 8.0% |
| spruce meal (wood meal F140 from the company SPPS): | 3.4% |
| propylene glycol: | 73% |
| behenyltrimethylammonium chloride (GENAMIN KDMP from Clariant): | 3.3% |
| cetylstearyl alcohol: | 3.3% |
| dyes, fragrance | qs |
| propylene glycol: | qs 100%, i.e. about 75%) |

Example 4

Various anhydrous shampoo compositions according to the present disclosure were formulated. The formulations were as given in Table 1 below (as weight percentages relative to the total weight of the composition).

TABLE 1

| | 1 | 2 | 3 | 4 | 5 |
|---|---|---|---|---|---|
| Hollow microspheres of vinylidene chloride/acrylonitrile/methyl methacrylate copolymer expanded with isobutane (EXPANCEL 551 DE 40 d42 from the company Expancel) | 3.3 | 2.6 | 3.3 | 2.6 | 2 |
| Dye disodium salt of tartrazine: Yellow 5 (LCW) | 0.004 | 0.004 | 0.004 | 0.004 | 0.004 |
| Dye disodium salt of brilliant blue: Blue 1 (LCW) | 0.005 | 0.005 | 0.005 | 0.005 | 0.005 |
| Spruce meal (F140 from SPPS) | 10.2 | 11.9 | 10.3 | 11.9 | 12 |
| Fragrance | 0.5 | 0.5 | 0.5 | 0.5 | 0.5 |
| 96/4 mixture of the sodium salt of potato carboxymethylstarch and of ethanol (PRIMOGEL from the company DMV International) | 5.1 | 5.9 | 5.1 | 5.9 | 6 |
| Disodium lauryl sulfosuccinate: REWOPOL SB F 12 P (Degussa) | | | | 17.9 | 17.9 |
| Sodium lauryl sulfate powder: TEXAPON Z 95 P (Cognis) | 15.3 | 17.9 | 15.3 | | |
| Polyethylene glycol 400 | qs 100 (about 65.6) | | | | |
| Glycerol | | 40.8 | 43.7 | 40.8 | 41.1 |
| Propylene glycol | | qs 100 (about 20.4) | qs 100 (about 21.8) | qs 100 (about 20.4) | qs 100 (about 20.5) |

All these compositions had a pleasant and supple, more or less firm texture, but broke down easily upon contact with water, generating a heating effect.

Example 5

Various anhydrous rinse-out care compositions according to the present disclosure were formulated. The formulations were as given in Table 2 below (on a weight basis relative to the total weight of the composition).

TABLE 2

| | 6 | 7 | 8 | 9 | 10 | 11 |
|---|---|---|---|---|---|---|
| Hollow microspheres of vinylidene chloride/acrylonitrile/methyl methacrylate copolymer expanded with isobutane (EXPANCEL 551 DE 40 d42 from the company Expancel) | 4.35 | 3.5 | 4.2 | 3.4 | 3.8 | 3.5 |
| Cetylstearyl alcohol: LANETTE ® O (Cognis) | | | | | 1.6 | 1.2 |
| Myristyl/cetyl/stearyl myristate/palmitate/stearate mixture: MIRACETI (Laserson) | | | | | 0.8 | 0.6 |
| Spruce meal (F140 from SPPS) | 1.9 | 5.3 | 2.9 | 7.8 | 5.3 | 10.4 |
| 96/4 mixture of sodium salt of potato carboxymethyl starch and of ethanol (PRIMOGEL from the company DMV International) | 4.45 | 12.4 | 6.7 | 18.4 | 12.3 | 24.2 |
| Behenyl trimethyl-ammonium chloride: GENAMIN KDMP (Clariant) | 4.0 | 3.5 | | | 3.2 | 2.5 |
| Dicetearoyléthyl-hydroxyethyl-methylammonium methosulfate/cetearyl alcohol: DEHYQUART F 75 (Cognis) | | | | 3.9 | 3.2 | |
| Propylene glycol | qs 100 (about 85.3) | qs 100 (about 75.3) | qs 100 (about 82.3) | qs 100 (about 67.2) | qs 100 (about 73.0) | qs 100 (about 57.6) |

All these compositions had a pleasant and supple, more or less firm texture, and broke down easily upon contact with water, generating a heating effect.

What is claimed is:

1. An anhydrous cosmetic composition comprising
at least one organic structuring agent,
at least one modified starch,
at least one wood meal,
at least one surfactant, and
at least one anhydrous liquid phase,
wherein the at least one wood meal is present in a total amount ranging from 1.5% to 15% by weight relative to the total weight of the composition; and
wherein the at least one modified starch is present in a total amount ranging from 3% to 25% by weight relative to the total weight of the composition.

2. The composition according to claim 1, wherein the at least one organic structuring agent comprises at least one type of particles.

3. The composition according to claim 2, wherein the at least one type of particle is chosen from thermoplastic material particles chosen from polyamides, polymers comprising at least one monomer chosen from acrylonitrile, vinylidene chloride, vinyl chloride, optionally expanded acrylic, and optionally expanded styrene monomer, and microporous microspheres.

4. The composition according to claim 3, wherein the at least one type of particle is chosen from hollow particles of an expanded copolymer of vinylidene chloride and acrylonitrile, and hollow particles of an expanded copolymer of vinylidene chloride, acrylonitrile and methyl methacrylate.

5. The composition according to claim 1, wherein the at least one organic structuring agent is present in a total amount ranging from 1% to 10% by weight relative to the total weight of the cosmetic composition.

6. The composition according to claim 5, wherein the at least one organic structuring agent is present in a total amount ranging from 3% to 4% by weight relative to the total weight of the cosmetic composition.

7. The composition according to claim 1, wherein the at least one modified starch is chosen from potato starches.

8. The composition according to claim 1, wherein the at least one wood meal is spruce meal.

9. The composition according to claim 1, wherein the at least one modified starch and the at least one wood meal are present in a total combined amount ranging from 10% to 20% by weight relative to the total weight of the composition.

10. The composition according to claim 1, wherein the at least one modified starch is present in a total amount ranging from 4% to 15% by weight relative to the total weight of the composition.

11. The composition according to claim 1, wherein the at least one surfactant is chosen from cationic, anionic, nonionic, and amphoteric surfactants.

12. The composition according to claim 1, wherein the at least one surfactant is present in a total amount ranging from 1% to 40% by weight relative to the total weight of the composition.

13. The composition according to claim 12, wherein the at least one surfactant is present in a total amount ranging 4% to 20% by weight relative to the total weight of the composition.

14. The composition according to claim 1, wherein the at least one anhydrous liquid phase is chosen from monoalcohols, polyols, and fatty substances.

15. The composition according to claim 1, wherein the at least one anhydrous liquid phase is present in a total amount of at least 50% by weight relative to the total weight of the composition.

16. The composition according to claim 15, wherein the at least one anhydrous liquid phase is present in a total amount ranging from 50% to 95% by weight relative to the total weight of the composition.

17. A method for cleansing and/or conditioning keratin materials, comprising applying at least one anhydrous cosmetic composition to the keratin materials, wherein the at least one anhydrous composition comprises
- at least one organic structuring agent,
- at least one modified starch,
- at least one wood meal,
- at least one surfactant, and
- at least one anhydrous liquid phase,
- wherein the at least one wood meal is present in a total amount ranging from 1.5% to 15% by weight relative to the total weight of the composition; and
- wherein the at least one modified starch is present in a total amount ranging from 3% to 25% by weight relative to the total weight of the composition.

* * * * *